US008261738B2

(12) United States Patent
Denyer et al.

(10) Patent No.: US 8,261,738 B2
(45) Date of Patent: Sep. 11, 2012

(54) APPARATUS AND METHOD FOR MAINTAINING CONSISTENCY FOR AEROSOL DRUG DELIVERY TREATMENTS

(75) Inventors: Jonathan S. H. Denyer, Chichester (GB); Ivan R. Prince, Chichester (GB); Anthony Dyche, Hayling Island (GB)

(73) Assignee: Respironics Respiratory Drug Delivery (UK) Ltd., Tangmere, Chichester ( * ) Notice: Subject to any disclaimer, the term of this patent is extended or adjusted under 35 U.S.C. 154(b) by 1089 days.

(21) Appl. No.: 12/175,486

(22) Filed: Jul. 18, 2008

(65) Prior Publication Data

US 2009/0025718 A1 Jan. 29, 2009

Related U.S. Application Data

(60) Provisional application No. 60/961,727, filed on Jul. 24, 2007.

(51) Int. Cl.
*A61M 15/00* (2006.01)

(52) U.S. Cl. .................................................. 128/203.14

(58) Field of Classification Search .............. 128/203.14
See application file for complete search history.

(56) References Cited

U.S. PATENT DOCUMENTS 4,550,726 A * 11/1985 McEwen .................. 128/202.22
5,022,587 A 6/1991 Hochstein
5,331,953 A 7/1994 Andersson et al.
5,608,647 A * 3/1997 Rubsamen et al. ........... 700/281
5,655,523 A 8/1997 Hodson et al.
5,884,620 A 3/1999 Gonda et al.
6,546,927 B2 * 4/2003 Litherland et al. ....... 128/200.16
6,571,793 B1 6/2003 Nilsson
6,584,971 B1 * 7/2003 Denyer et al. ............ 128/203.14
6,640,804 B2 11/2003 Ivri et al.
6,830,046 B2 12/2004 Blakley et al.
6,845,770 B2 1/2005 Klimowicz et al.
6,863,224 B2 3/2005 Terada et al.
6,971,383 B2 12/2005 Hickey et al.
7,040,549 B2 5/2006 Ivri et al.
7,077,125 B2 7/2006 Scheuch
7,167,776 B2 1/2007 Maharajh et al.
2002/0185125 A1 * 12/2002 Klimowicz et al. ...... 128/200.16
2003/0039742 A1 2/2003 Qiu et al.
2003/0159693 A1 8/2003 Melker et al.
2003/0217747 A1 11/2003 Hickle et al.
2004/0123864 A1 * 7/2004 Hickey et al. ............ 128/203.12
2005/0155602 A1 7/2005 Lipp
2005/0217666 A1 * 10/2005 Fink et al. ................ 128/200.14
2005/0229931 A1 10/2005 Denyer et al.
2005/0284469 A1 12/2005 Tobia et al.
2006/0162723 A1 7/2006 Selzer et al.
2006/0201499 A1 9/2006 Muellinger et al.
2007/0017505 A1 1/2007 Lipp et al.

OTHER PUBLICATIONS

U.S. Appl. No. 10/535,867, Denyer et al.

* cited by examiner

*Primary Examiner* — Loan Thanh
*Assistant Examiner* — Shila Jalalzadeh Abyane

(57) ABSTRACT

An aerosol drug delivery apparatus is provided. The apparatus may include a reservoir constructed to contain a predetermined dose of a liquid drug, an aerosol generator in communication with the reservoir, and a power source arranged to deliver power to the aerosol generator in order to produce an aerosolized form of the dose that can be administered to a patient. The apparatus may maintain consistent aerosol drug delivery treatments, for example, by way of a breath measuring mechanism that monitors the patient's breathing pattern during the administration of the dose and a controller configured to vary the power level at which the power source during the administration of the dose based on the monitored breathing pattern.

22 Claims, 5 Drawing Sheets

DRUG DELIVERY DEVICE 100

105 120 115 L 125

APPARATUS AND METHOD FOR MAINTAINING CONSISTENCY FOR AEROSOL DRUG DELIVERY TREATMENTS

CROSS-REFERENCE TO RELATED APPLICATIONS

This application claims priority under 35 U.S.C. §119(e) from provisional U.S. patent application No. 60/961,727 filed Jul. 24, 2007, the entire contents of which are incorporated herein by reference.

BACKGROUND OF THE INVENTION

1. Field of the Invention

The present invention relates to maintaining consistency for aerosol drug delivery treatments, and in particular, to varying power of an aerosol drug delivery device during treatment to maintain a consistent treatment time.

2. Description of Related Art

Aerosol drug delivery devices are often used in medical treatment to provide drugs in a form that can be inhaled by a patient. Drugs in powder, liquid, or other forms may be aerosolized using various techniques (e.g., using a piezoelectric member) to enable the drug to be absorbed through the patient's air passage. As such, aerosol drug treatments may be administered for respiratory ailments (e.g., asthma) or other treatments where a patient inspires drugs while breathing.

Aerosol drug treatments are typically designed to administer a specific dosage of drug over a given period of time. Maintaining uniformity in treatment (i.e., dosage and treatment time) can often be a factor in the effectiveness of the treatment or the marketability of a treatment system, among other things. Existing systems and techniques for administering aerosol drug treatments, however, often fail to adequately account for various factors that may interfere with uniformity in treatment. For example, an administered drug dosage or treatment duration may be non-uniform due to variations in a breathing pattern of a patient, properties of a drug delivery device (e.g., output rate), or other factors.

Existing systems suffer from these and other problems.

SUMMARY OF THE INVENTION

According to various aspects of the invention, a method for maintaining consistency for aerosol drug delivery treatments is provided. A predetermined dose of an aerosolized drug may be administered to a patient using an aerosol generator that operates at an initial power level. The patient's breathing pattern may be monitored during the administration of the dose, and a consistent treatment time may be maintained by varying the power level at which the aerosol generator operates during the administration of the dose based on the monitored breathing pattern.

According to another aspect of the invention, a method for maintaining consistency for aerosol drug delivery treatments is provided. A predetermined dose of an aerosolized drug may be administered to a patient using an aerosol generator that operates at an initial power level. An elapsed treatment time for the administration of the dose may be monitored, and the power level at which the aerosol generator operates may be increased based upon a relationship between the elapsed treatment time and a nominal treatment time.

According to another aspect of the invention, an aerosol drug delivery apparatus may maintain consistency for aerosol drug delivery treatments. For example, the apparatus may include a reservoir constructed to contain a predetermined dose of a liquid drug, an aerosol generator in communication with the reservoir, and a power source arranged to deliver power to the aerosol generator in order to produce an aerosolized form of the dose that can be administered to a patient. A breath measuring mechanism may monitor the patient's breathing pattern during the administration of the dose, and a controller may vary the power level at which the power source operates during the administration of the dose based on the monitored breathing pattern.

According to another aspect of the invention, an aerosol drug delivery apparatus may be used to diagnose poor patient respiration. The apparatus may include a reservoir constructed to contain a predetermined dose of a liquid drug, an aerosol generator in communication with the reservoir, and a power source arranged to deliver power to the aerosol generator in order to produce an aerosolized form of the liquid drug that can be administered to a patient. A breath measuring mechanism may monitor the patient's breathing pattern during administration of the dose, and a perceptible output device may provide a perceptible output when the monitored breathing pattern indicates that the patient has a poor breathing pattern.

According to another aspect of the invention, an aerosol drug delivery apparatus may be self-diagnosing. The apparatus may include a reservoir constructed to contain a predetermined dose of a liquid drug, an aerosol generator in communication with the reservoir, and a power source arranged to deliver power to the aerosol generator in order to produce an aerosolized form of the liquid drug that can be administered to a patient. A clock may monitor an amount of time that the aerosol generator is active during administration of the dose, and a perceptible output device may provide a perceptible output indicating that a mesh in the drug delivery apparatus should be changed based on a relationship between the monitored amount of time and a nominal amount of time that the aerosol generator should have been active during the administration of the dose.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
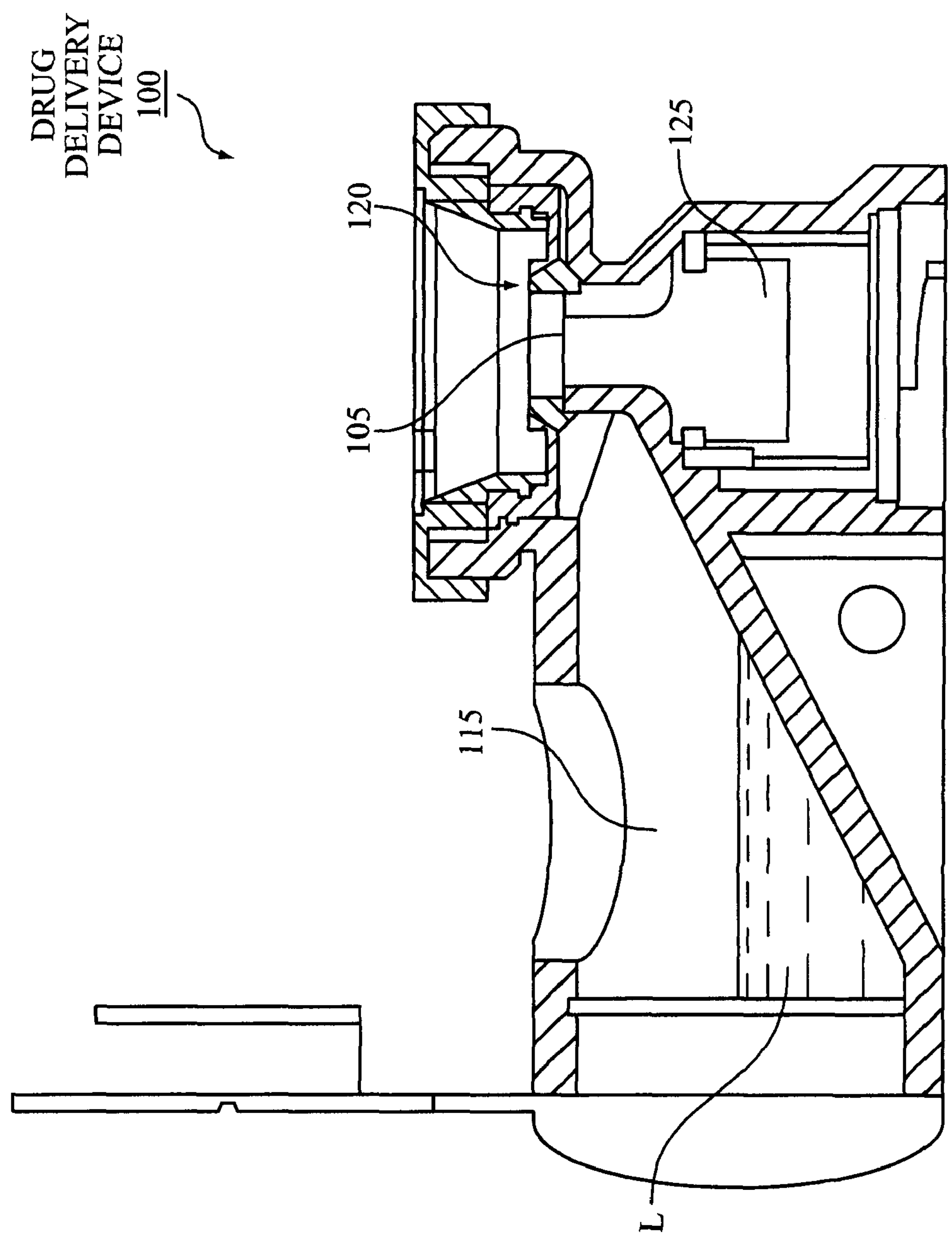
FIG. 1 illustrates an exemplary aerosol drug delivery device according to various aspects of the invention.

According to various aspects of the invention, as illustrated in FIG. 1, for example, an aerosol drug delivery device 100 may be used to administer an aerosol form of a liquid drug L for inspiration by a patient. For example, device 100 may include a reservoir 115 for containing a liquid drug L and an aerosol generator 120.

The aerosol generator 120, in one embodiment, may take the form of a mesh member 105 in combination with a horn oscillating member 125 for nebulizing or otherwise aerosolizing the liquid drug L. However, as discussed in more detail later, this type of aerosol generator 120 is a non-limiting example of the many different types of aerosol generators that can be used within the scope of the present invention. The mesh member 105 is, in one embodiment, may be mounted to an end surface of a distal end of the horn oscillating member 125. The drug delivery device 100 may incorporate any suitable power source (as will be discussed later) to electrically drive the horn oscillating member 125. As such, the horn oscillating member 125 may force the liquid L through a plurality of fine apertures or pores in mesh member 105, thereby producing an aerosolized form of liquid drug L that can be inspired by a patient.

The reservoir 115 can be any chamber, container, or canister that may contain a dosage of liquid drug. In various implementations, aerosol generator 120 and reservoir 115 device 100 may be constructed and arranged as described in U.S. Pat. No. 6,863,224 ("the '224 patent"), issued Mar. 8, 2005, entitled "Liquid Spray Device," the disclosure of which is hereby incorporated by reference in its entirety. It should be emphasized, however, that the '224 patent discloses but one example of the type of aerosol generator and reservoir that can be employed with the teachings of the present invention, as will be apparent from the farther descriptions herein.

Figure 2:
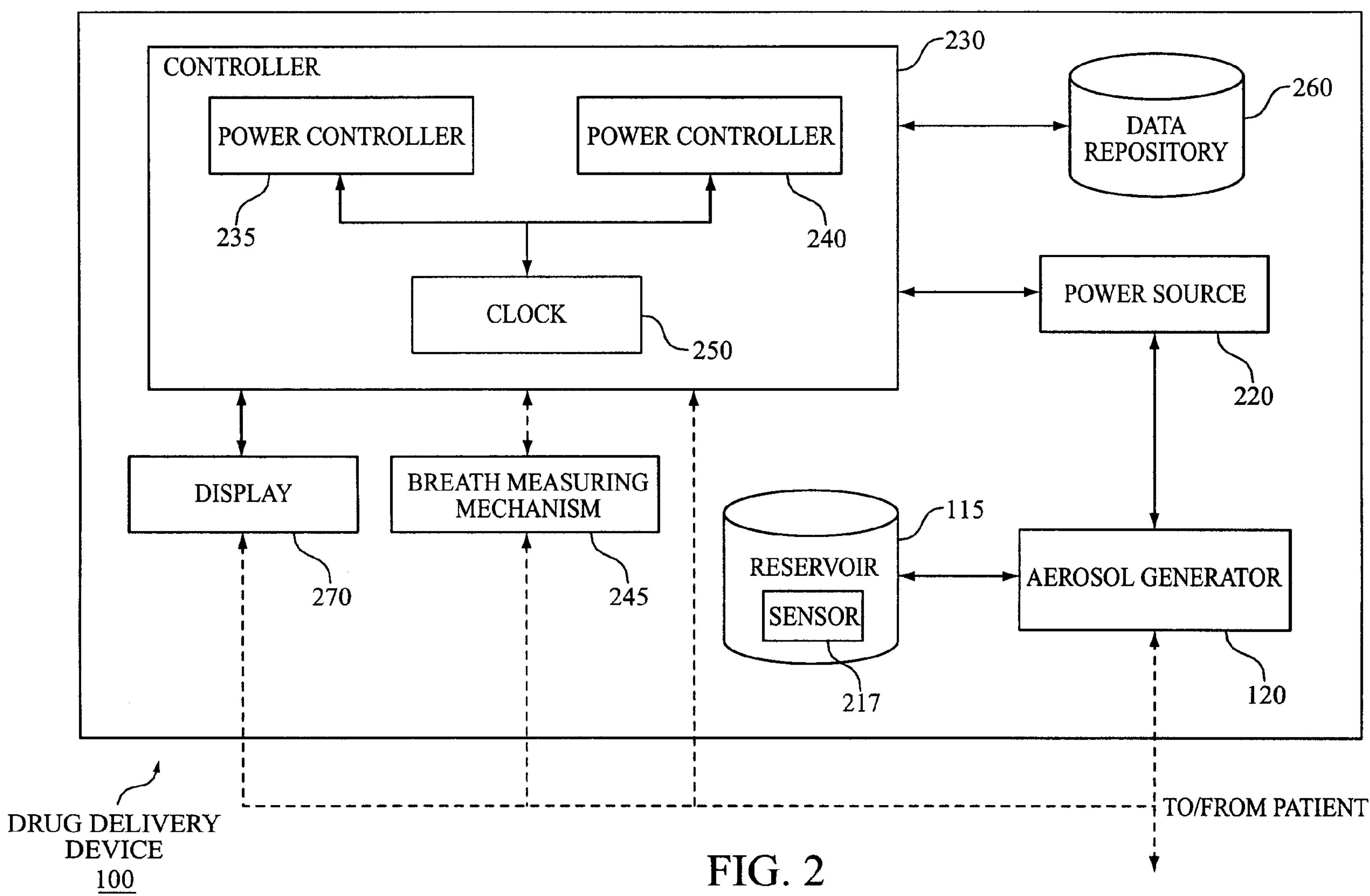
FIG. 2 illustrates an exemplary system for maintaining consistency for aerosol drug delivery treatments according to various aspects of the invention.

FIG. 2 is a schematic diagram representing various components of the exemplary drug delivery device 100 of FIG. 1, and which may be configured to maintain consistent treatment times for aerosol drug delivery treatments in accordance with various aspects of the invention. In one embodiment, the reservoir 115 cooperates with or includes a sensor 217 that can be used to determine whether the liquid drug L in the reservoir 115 has been fully depleted, as will be described in more detail later.

The aerosol generator 120 may be in electrical communication with power source 220, which drives the operation (e.g., nebulizing action) of the aerosol generator 120. For example, in the embodiment where the aerosol generator 120 comprises mesh 105 and horn oscillating member 125, the power source 220 drives the operation (e.g., on/off) of the horn oscillating member 125 and the power level applied to the horn oscillating member 125.

Drug delivery device 100 may administer the drug dosage in reservoir 115 by aerosolizing the drug dosage contained therein over successive aerosol pulses for inspiration by a patient (e.g., one pulse per patient inhalation). For example, power source 220 may deliver successive pulses of power to aerosol generator 120, causing the horn oscillating member 125 to produce corresponding pulses of aerosolized drug (e.g., liquid droplets or vapor). Pulses of power (and corresponding pulses of aerosolized drug) may continue to be delivered until all liquid (i.e., the entire dose) in reservoir 115 has been aerosolized (and ideally inhaled by the patient), thereby completing the administered treatment.

As noted above, aerosol generator 120 may produce the aerosolized form of the liquid drug L using any type of nebulizer or aerosol generating mechanism that can turn the liquid drug L into aerosol and/or droplets that can be inhaled by the patient. For example, as illustrated in FIG. 1, liquid drug L disposed in reservoir 115 may reach a proximal point of contact between a distal end of oscillating horn member 125 and mesh 105 (e.g., a metallic or non-metallic screen having a plurality of fine apertures). Referring back to FIG. 2, the power source 220 may deliver a pulse of power to aerosol generator 120, causing the horn 125 to vibrate and drive the liquid drug through the mesh 105, detaching the liquid into an aerosolized form. It will be apparent, however, that various other aerosol generators 120 may be used, including jet nebulizers, vibrating meshes, vibrating horns, nozzles that use Raleigh breakup theory, piezoelectric crystal technology, or other nebulizing devices or techniques known in the art. It should be appreciated that these are non-limiting examples of the type of aerosol generators that can be used with the present invention, and that any suitable device that can nebulize or aerosolize a liquid drug for this application can be used.

As can be appreciated from the discussion above, aerosol generator 120 may be configured to receive pulses of power from power source 220 until all of the liquid in the chamber 115 has been aerosolized for inspiration by the patient. As such, a uniform drug dosage may be administered in every treatment instance. For various reasons, however, aerosol generator 120, in itself may not necessarily maintain a uniform duration of treatment for every treatment. For example, a breathing pattern of a patient (e.g., an inhalation to exhalation ratio, a breathing frequency, etc.) may impact a rate of drug administration, potentially impacting treatment time. In another example, the mesh 105 of aerosol generator 120 may become dirty over a course of treatment, or a reusable mesh may become dirtier over a course of successive treatments, or meshes may be interchanged between treatments, or the mesh may degrade over time, all of which may be among contributing factors potentially impacting treatment time (e.g., by reducing a rate at which generator 120 outputs the aerosolized drug).

Accordingly, as shown in FIG. 2, a controller 230 is coupled to power source 220 to minimize variations in treatment time. Controller 230 may be a hardware controller (e.g., an electrical circuit or microprocessor), a software controller (e.g., computer-executable instructions), or any suitable combination thereof. Controller 230 may vary a level of power delivered to aerosol generator 120 by the power source 220 based on various factors, including a breathing pattern of a patient, a cleanliness or dirtiness of a mesh, or variations in an output rate of generator 120, among other things.

Controller 230 may include a clock 250 for tracking an elapsed duration of a treatment, a power controller 235, and a pulse controller 240 (e.g., combinations of hardware components and computer-executable instructions) for electronically controlling power levels and pulse lengths applied by the power source 220 to the aerosol generator 120. It should be appreciated that the controller 230 can be considered a single device incorporating the functionalities of each of clock 250, power controller 235, and pulse controller 240. Alternatively, each of the elements 250, 235, and 240 may be considered to be separate components or modules that may be provided separately, or outside of controller 230.

The drug delivery device 100 may also include a breath measuring mechanism 245, operatively connected with controller 230, and which is operable to monitor or otherwise measure a patient's breathing pattern. The breathing pattern may include measurements of one or more of the patient's tidal volume, flow rate, inhalation rate, exhalation rate, a ratio of inhalation to exhalation rates, or other characteristics of a patient's breathing. In various implementations, the breath measuring mechanism 245 can include a pressure sensor for detecting the pressure within an atomizing section of a nebulizer, a respiratory valve, a patient port, or other suitable structure for measuring the patient's breathing pattern. As such, in various embodiments, the patient's breathing pattern (e.g., inhalation duration) could be measured by triggering a timer based on the pressure detected by the sensor and measuring the duration of inspiration. As another example, the breath measuring mechanism can employ a sensor that measures gas concentration or light dispersion, to measure a concentration of aerosolized medication in a mouthpiece (or elsewhere), in conjunction with a flow sensor, in order to estimate an amount of medication inhaled per breath. In one embodiment, the breathing pattern may be measured using techniques and structures described in U.S. Pat. No. 6,584,971 ("the '971 patent"), issued Jul. 1, 2003, entitled "Drug Delivery Apparatus," the disclosure of which is hereby incorporated by reference in its entirety. It will be appreciated, however, that the '971 patent illustrates but one example of a way in which to measure a patient's breathing pattern, and that other structures or techniques can be used.

Controller 230 may be coupled to a data repository 260 (e.g., a built-in memory, a removable media or memory, etc.). The data repository 260 may be capable of storing settings that describe the treatment to be administered and a log of administered treatment data to assist in performing diagnostics or maintenance. Any of the settings may be manually input to data repository 260 through an input interface, or may be pre-coded into the data repository 260. The settings in data repository 260 may include information relating to nominal treatment duration, liquid drug dosage, and/or power levels, among other information for maintaining consistency for an aerosol drug delivery treatment. For instance, the settings may relate to a nominal output rate for the mesh (e.g., expressed in milliliters per minute), which may be defined as a function of one or more of the mesh grading, a nominal power setting, a medication chamber dosage (or chamber volume) (e.g., milliliters), and a target treatment duration, or any combination thereof. Further, the settings may include additional information used to vary a power level delivered to aerosol generator 120, including a current power setting, a maximum power setting, a minimum power setting, threshold inhalation to exhalation ratios, and deltas for increasing or decreasing power, among other things.

Clock 250 may begin when a treatment starts, thereby actively measuring an elapsed time of the treatment. Each time that the patient breathes during the treatment, breath measuring mechanism 245 may measure one or more of the patient's inhalation duration, exhalation duration, a ratio of the inhalation to exhalation durations, tidal volume, flow rate, any combination of the foregoing, or other respiration characteristics to determine the patient's current breathing pattern (e.g., as described in the incorporated '971 patent). Based on these measurements, pulse controller 240 may determine an optimal length of a pulse delivered by power source 220 to aerosol generator 120. The optimal duration for a pulse may last from when an inhalation begins (or shortly thereafter) until a point in the inhalation when the remaining volume to be inspired equals the estimated end volume (e.g., the volume of the patient's upper airway). The pulse would then cease, allowing the remaining volume to be cleared from aerosol generator 120 and inspired into the patient's lungs. For example, in various other implementations, the length of a pulse may be determined as described in the '971 patent (i.e., Pulse time=(average inhalation time)×(average tidal volume−end volume)/(average tidal volume)). It will be appreciated, however, that the '971 patent provides but one example of a technique for determining pulse length, and that other methods may be used without departing from the scope and spirit of the invention. For example, various implementations may control the pulse length as described in co-pending U.S. patent application Ser. No. 10/535,867, entitled "Inhalation Method and Apparatus," filed Nov. 20, 2003, the disclosure of which is hereby incorporated by reference in its entirety. In such implementations, the pulse length may be controlled to end a predetermined amount of time prior to when the patient is expected to stop inhaling, such that a period of time remains at the end of the breath to allow for sedimentation of the aerosol.

Upon measuring the patient's breathing pattern (e.g., inhalation duration, exhalation duration, ratio of the inhalation to exhalation durations, tidal volume, end volume, etc.), the pattern may be provided to power controller 235 for determining whether to vary a power level for the pulse delivered in a subsequent breath (e.g., based a relationship between the breathing pattern and threshold inhalation to exhalation ratios, as will be described herein). Further still, power controller 235 may use the measured elapsed treatment time, as measured by clock 250, to determine whether to increase the power level for the subsequent pulse. As such, various techniques may be used by power controller 235 to control a time for a treatment by determining whether to increase and/or decrease the power level during the treatment (e.g., to maintain consistent treatment times, reduce treatment times, increase treatments, achieve a target treatment time, or otherwise), as described in greater detail in FIGS. 3-4 below.

Figure 3:
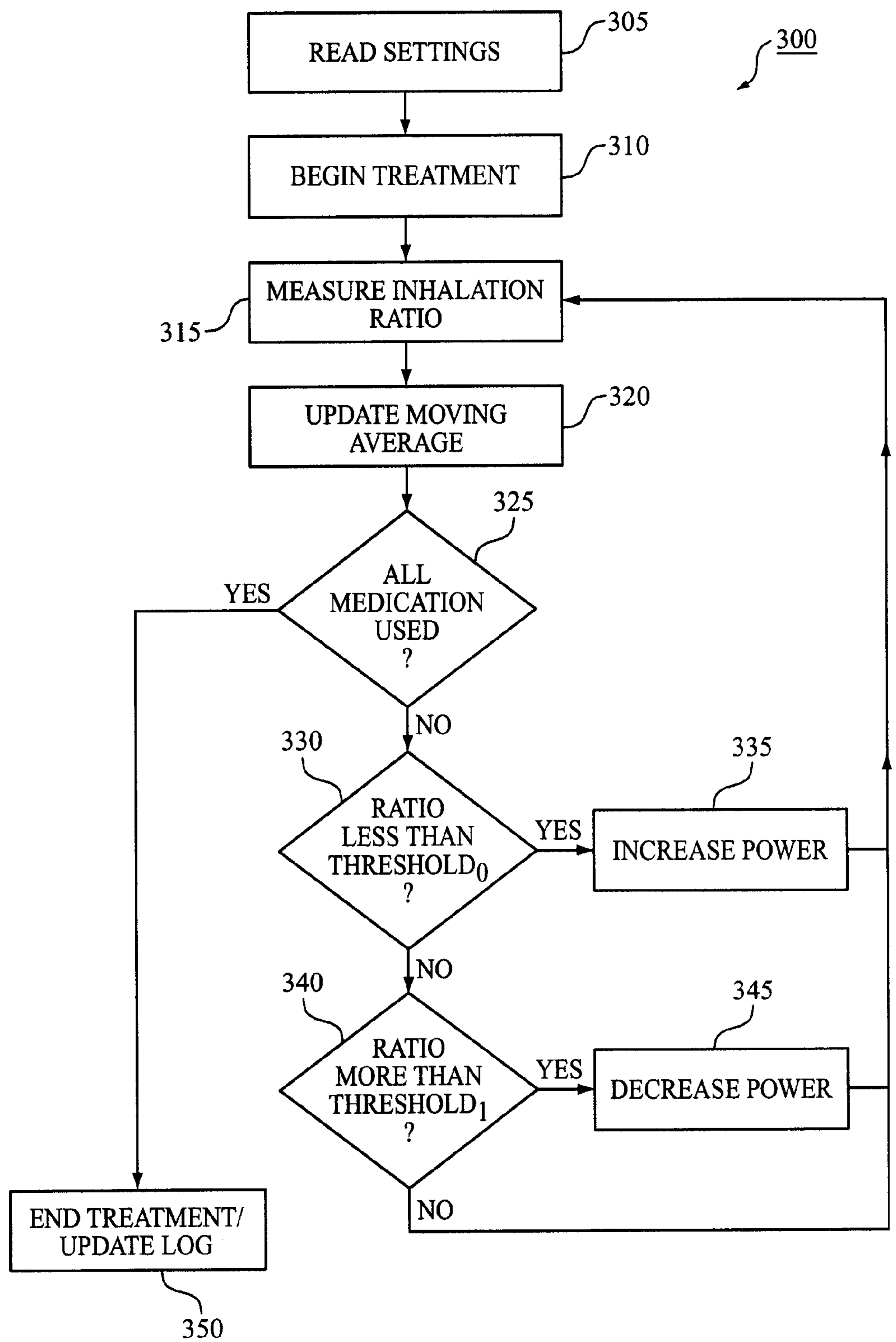
FIGS. 3-4 illustrate exemplary methods for maintaining consistency for aerosol drug delivery treatments according to various aspects of the invention.

Referring to FIG. 3, an exemplary method 300 for maintaining consistency for aerosol drug delivery treatments is illustrated. Method 300 may be used to vary a power level of aerosol drug delivery device 100 during treatment to maintain a consistent time for the treatment. For example, treatment duration may depend on a patient's breathing pattern, and method 300 may vary the power level in response to the breathing pattern to maintain a consistent treatment time, as described in greater detail below.

As an initial operation, one or more settings may be read at operation 305 (e.g., from settings stored in data repository 260, or otherwise) to initialize an aerosol drug treatment. Alternatively, the settings may be input manually into the data repository 260 or other memory in the drug delivery device 100. The settings may include information relating to the treatment, including a dosage of drug for the treatment (e.g., dependent on a quantity of drug in a medication chamber of the drug delivery device or physical volume of the reservoir 115), a target treatment duration, a mesh grading, and a nominal power level, among other things. As such, the treatment information may be used to calculate a nominal output rate (e.g., milliliters per minute) and a target pulse proportion (e.g., a proportion of each minute to be spent delivering aerosol pulses) for the aerosol drug treatment. Moreover, the settings read in operation 305 may include parameters for varying the power level during the treatment, including, among other things, minimum and maximum power levels, threshold inhalation to exhalation ratios for triggering changes in power levels, and variables for indicating how much to increase and/or decrease the power levels in any iteration.

Having all parameters and settings for administering and controlling treatment, input into, or otherwise stored or contained in, the data repository 260 or other memory, the treatment may begin at operation 310. When the treatment begins at operation 310, the power level delivered by power source 220 to the aerosol generator 120 may be set to the nominal power level. In various implementations, however, the nominal power level may be subject to variation based on log data from data repository 260 relating to one or more previous treatments. For example, when a patient exhibits a poor breathing pattern (e.g., by spending comparatively less time inhaling than normal), the nominal power setting may be increased to account for treatment otherwise likely to extend beyond the nominal treatment time. Other variations may be used, such as decreasing the nominal power setting when a patient has a longer than normal inhalation pattern, or otherwise, as will be apparent.

Over a course of the treatment, a patient's breathing pattern may be actively monitored. For instance, operation 315 includes measuring the patient's inhalation to exhalation ratio on a breath-by-breath basis, while operation 320 includes updating the running moving average of the inhalation ratio to reflect a most recent breath. Thus, the power level of the aerosol generator 120 may be dynamically adjusted for each breath, on a breath-by-breath, basis in response to any changes that occur to the breathing pattern. The change for any one breath may be based on a single prior breath, or on a plurality of prior breaths. In another embodiment, the power level of the aerosol generator 120 may by dynamically adjusted for a predetermined number of future breaths, based on only the preceding breath, or based on a plurality of prior breaths. In one embodiment, treatment time may be dependent upon a proportion of every minute that the aerosol generator 120 delivers aerosol pulses, which may further depend on a ratio of time that the patient spends inhaling versus exhaling. The inhalation to exhalation ratio may have a substantial effect on treatment time because a length of each pulse may be keyed to the ratio.

Each aerosol pulse may begin when an inhalation begins, or shortly thereafter (e.g., within one second from when inhalation begins), while ending prior to when the inhalation ends, thus leaving a period of time for the aerosol to deposit in the patient's body. As such, in one embodiment, the pulse length may last between approximately fifty and eighty percent of an inhalation, depending on the ratio (e.g., a patient that takes many short inhalations may receive proportionally shorter pulses and more deposit time than a patient that takes long inhalations). Exemplary techniques for controlling the pulse length based on breathing pattern may include those described in the '971 patent.

Accordingly, an inhalation to exhalation ratio may be a significant factor affecting treatment duration, as the treatment may be longer for patients having comparatively low inhalation to exhalation ratios, and vice versa. Thus, consistent treatment times may be maintained by increasing power levels delivered to aerosol generator 120 to compensate for a patient having a poor breathing pattern, or decreasing power levels delivered to aerosol generator 120 to compensate for a patient having a strong breathing pattern, ensuring that a quantity of aerosol generated per minute remains close to the desired nominal output rate.

Throughout the treatment, operation 320 may maintain a running moving average of the inhalation to exhalation ratio. The ratio may be measured by the controller 230 in conjunction with the breath measuring mechanism 245, and a moving average of the ratio, measured over a predetermined number of breaths (e.g., three breaths) may be determined by the controller 230 and stored in data repository 260 or other memory in the drug delivery device. For example, in various implementations, the moving average may be based on a limited number of breaths to ensure the moving average reflects a current breathing pattern. As various examples, a patient may experience an asthmatic attack during treatment, or drug absorption may improve a patient's respiratory strength, or other variations may occur such that the current breathing pattern may change dynamically over the course of treatment. As such, limiting a number of breaths factoring into the moving average may result in a more accurate assessment of the current breathing pattern. It will be apparent, however, that the number of breaths may be suitably increased or decreased when appropriate, or certain treatment types may include all breaths in the moving average without departing from the scope of the invention.

In operation 325, a determination is made as to whether all medication in the reservoir 115 has been administered. For example, in various implementations, the sensor 217 can detect the presence (or absence) of liquid in the reservoir 115. The sensor 217 may comprise any device for measuring the presence or absence of liquid, or the amount of liquid, in the reservoir 115. For example, a light obstruction or scattering sensor, an ultrasound or radio wave transmission time sensor, a sensor that measures electrical capacitance of air, a float switch, or other known sensors that can detect the presence of or absence of liquid can be used. In another embodiment, the sensor 217 may be constructed and arranged to determine changes in characteristics (e.g., changes in current or voltage) of an ultrasonic drive circuit for driving the horn or aerosol generator 120, where the changes are attributable to the depletion of the liquid from the reservoir 115.

As described in the incorporated '971 patent, the sensor 217 can be used to determine when the treatment should end (e.g., by detecting the absence of liquid in the reservoir 115). When all medication in the reservoir 115 has been administered, as determined by the sensor 217, this means that the prescribed dosage of drug has been administered, and the sensor 217 may send a signal to the controller 230 to indicate that treatment can be terminated in operation 350 (e.g., by cutting power to the aerosol generator 120). Further, operation 350 may update a log or generate a record of the treatment in data repository 260 for further analysis or diagnosis, among other things, as described in greater detail below.

However, when determination operation 325 determines that additional medication remains to be administered (e.g., when the sensor 217 detects the presence of additional medication in reservoir 115), treatment will continue, while inhalation/exhalation ratio determinations 330 and 340 determine whether to increase and/or decrease the power level (at operations 335 or 345) in subsequent pulses. For example, the inhalation/exhalation ratio determinations made in operations 330 and 340 may be based on a breathing model reflecting a typical patient inhalation to exhalation ratio, varying between approximately 1:1 and 1:2 (i.e., some patients may spend twice as much time exhaling as other patients in proportion to inhalation time).

As such, when it is determined at operation 330 that the proportion of inhalation time to exhalation time has fallen below a first threshold (i.e., $\text{Threshold}_0$ reflecting a poor breathing pattern), through use of the breath measurement mechanism 245, the power level may be increased at operation 335 by a first delta. By contrast, when the inhalation/exhalation time proportion has not fallen below $\text{Threshold}_0$, but exceeds a second threshold (i.e., $\text{Threshold}_1$ reflecting a strong breathing pattern), the power level may be decreased at operation 345 by a second delta. For example, the power level may be increased or decreased via power controller 235, which may provide an electronic signal to power source 220 that regulates the power level delivered to aerosol generator 120. In various implementations, $\text{Threshold}_0$ and $\text{Threshold}_1$ may be based on any suitable model, and the first delta may be set to be larger than the second delta to reflect a poor breathing pattern having a greater impact on treatment time than strong breathing patterns. Otherwise, the breathing pattern may reflect typical inhalation to exhalation ratios, in which case processing returns to operation 315 without changing the power level, awaiting another breath to measure.

Furthermore, power levels may be constrained within an appropriate range, defined by a predetermined minimum level and a predetermined maximum level. The minimum level may be defined to ensure that power continues to be delivered to the aerosol generator 120 as long as medication remains in the reservoir 115 (e.g., the minimum level may ensure that the device does not turn off, or that power does not go to zero). Similarly, the maximum power level may be defined to ensure that power circuitry does not become overloaded or otherwise interfere with proper operation of the device. Specific power levels may depend on a design or configuration of any given device, which is manufactured to have a maximum power output.

Upon sensor 217 determining that all medication has been used, thereby ending the treatment at operation 350, the log in data repository 260 may be updated in that operation 350. The log in data repository 260 may store information about each treatment administered for a patient. The stored treatment information may be downloaded to a personal computer or other suitable device, and may include, for each treatment, a total aerosol generator (e.g., a horn) actuation time, a total amount of time the patient spent inhaling, and a total amount of time the patient spent exhaling, among other things. In various implementations, one or more of the horn actuation time, the inhalation time, or the exhalation time may be rounded to a nearest second.

The log data in data repository 260 may be used to aid therapists in assessing diagnostics of a patient's treatment or to otherwise provide additional understanding regarding treatment. For example, the time spent inhaling and/or exhaling during treatments may be used to diagnosis a patient's breathing. Moreover, the log data may provide an indication of how actively power levels were varied during treatment to compensate for breathing patterns. For example, a proportion of time spent inhaling may be calculated (e.g., by dividing the time spent inhaling by the sum of the time spent inhaling and exhaling) to analyze breathing patterns and power changes, where a proportion of less than about forty percent may indicate that power was actively increased during various breaths, a proportion of between about forty percent and about forty-eight percent may indicate that power was subject to minimal net effects, and a proportion of greater than about forty-eight percent may indicate that power was actively decreased during various breaths. It will be appreciated, however, that these percentages and ranges thereof are exemplary only and can be varied for all patients, or on a patient-by-patient basis, or otherwise. Further still, the log may store codes used to provide feedback to the patient when a treatment has completed. For example, various codes may indicate whether the patient's breathing pattern during the treatment was normal, poor, strong, or otherwise (e.g., by displaying on a display connected to controller 230, an indication of the patient's breathing pattern based on the proportion of time spent inhaling and/or exhaling). In one embodiment, any of this information that may help a physician diagnose a patient may be sent by the controller 230 to a display 270, where the information can be read by the physician. The display 270 may be a liquid crystal display, a light emitting diode (LED) display, or other readable display. In another embodiment, the display 270 can be replaced by any device capable of providing a perceptible output. For example, a speaker can be used to provide an audible alert that may output a sound or voice recorded message diagnosing a certain condition (e.g., "poor breathing pattern").

Figure 4:
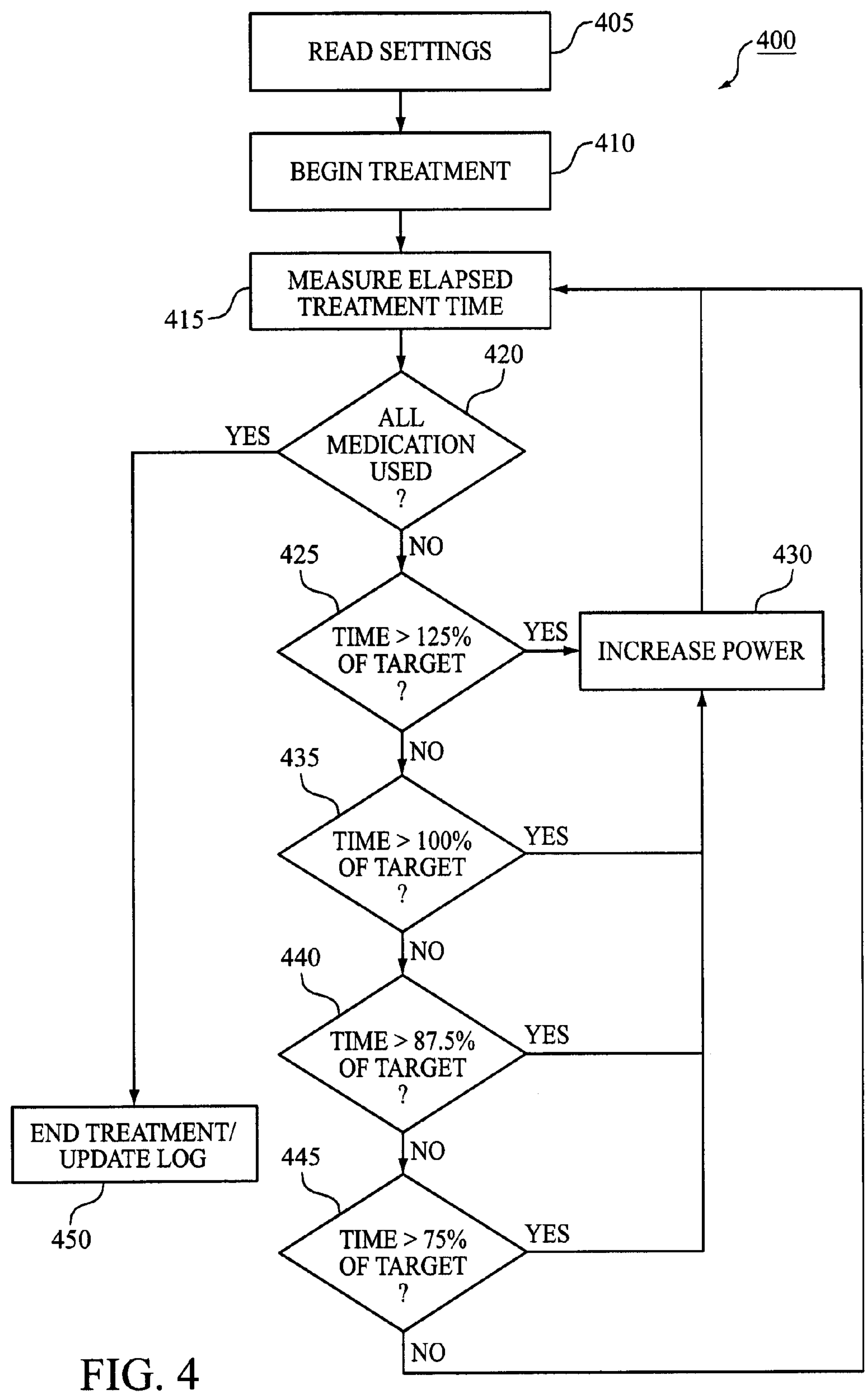

Referring to FIG. 4, another method 400 for maintaining consistency for aerosol drug delivery treatments is illustrated according to various aspects of the invention. Method 400 may be used to vary a power level delivered to the aerosol generator 120 during treatment to maintain a consistent time for the treatment. For example, a nominal treatment duration may depend on a nominal output rate for an aerosol drug delivery device (e.g., a function of mesh grading, drug dosage, and nominal power level). As such, method 400 may monitor an elapsed duration of a treatment, and may slowly increase the power level as a function of the nominal treatment time. Thus, method 400 may maintain the output rate as close as possible to the nominal rate, thereby achieving a consistent treatment time.

Beginning the method 400, one or more settings may be read at operation 405 (e.g., from settings stored in data repository 260, either preselected or manually input) to initialize an aerosol drug treatment. The settings may include information relating to the treatment, including a dosage of drug for the treatment (e.g., dependent on a total fill volume of the medication reservoir 115 (a preselected fixed volume), or input based upon a quantity of drug (the dose) actually placed in medication reservoir 115 of the drug delivery device 200), a target treatment duration, a mesh grading, and a nominal power level, among other things. Again, any one or more of the settings may be manually input to data repository 260 through an input interface, or may be pre-coded into the data repository 260. As such, the treatment information may relate to a nominal output rate (e.g., milliliters per minute) and a target pulse proportion (e.g., a proportion of each minute to be spent delivering aerosol pulses). As discussed above, in various instances a dirty mesh or an interchanging of meshes may cause an actual device output rate to vary from the nominal output rate.

Having the parameters and settings for administering and controlling treatment read at operation 405, the treatment begins at operation 410. After the treatment begins, an elapsed time of the treatment may be monitored at operation 405 (e.g., via clock 250). In addition, at operation 405 the power level delivered to the aerosol generator 120 may initially be set to the nominal power level (e.g., based on the read settings, or a manual input, a reactive mechanism based on previous treatments, etc.). By determining the nominal treatment duration when the settings are read at operation 405, the power level to the aerosol generator 120 may be increased when a treatment appears likely to exceed the target duration, thus compensating for a fall in device output rate. For example, whether or not all medication is used is determined at operation 420. If operation 420 determines (through sensor 217) that the reservoir 115 contains medication that must still be administered, and the elapsed time approaches the target treatment duration, it may be assumed that the device output rate has fallen below the nominal rate, or may potentially be below the nominal output rate (e.g., because of a dirty mesh). Rather than waiting for the elapsed time to pass the nominal treatment duration, however, the power level may be increased (at step 430 as discussed below), or otherwise ramped up slowly in advance of the treatment ending. As a result, when the mesh is dirty or otherwise functioning less than optimally, the treatment time can end in close proximity to the desired or nominal time, or at least closer to the nominal time in comparison with no increase in power supplied to the aerosol generator 120.

Accordingly, operation 445 increases the power if the elapsed time reaches 75% of nominal treatment time, operation 440 increases the power if the elapsed time reaches 87.5% of nominal treatment time, operation 435 increases the power if the elapsed time reaches 100% of nominal treatment time, and operation 425 increases the power if the elapsed time reaches 125% of nominal treatment time. Thus, the power level slowly increases towards the end of a treatment based on a relationship between elapsed treatment time and nominal treatment time. It should be appreciated, however, that the specific intervals illustrated herein are exemplary only, and that the selected intervals may be varied, or additional intervals may be substituted, as appropriate (e.g., the number of intervals could be doubled by halving the degree by which the power is increased). In one embodiment, drug delivery device 100 may include a predetermined number of power levels, and an output rate of the device may be a function of the power level. Accordingly, by increasing and/or decreasing the power level by a given amount, the output rate of the device can be controlled. In an exemplary illustration, the drug delivery device 100 may include a range of power levels as indicated in the following table, where each power level provides a device output rate that is a function of a default power level (e.g., level 8 in the illustrated table).

| Power Level | Percent Change in Output Rate from Default Power Level (e.g., Level 8) |
|---|---|
| 1 | 45.8% |
| 2 | 53.5% |
| 3 | 61.3% |
| 4 | 69.0% |
| 5 | 76.8% |
| 6 | 84.5% |
| 7 | 92.3% |
| 8 | 100.0% |
| 9 | 107.7% |
| 10 | 115.5% |
| 11 | 123.2% |
| 12 | 131.0% |
| 13 | 138.7% |
| 14 | 146.5% |
| 15 | 154.2% |

In another embodiment, rather than increasing the power to the aerosol generator 120 at predetermined intervals, it is contemplated that the power level may be increased continuously over time, either linearly or exponentially, starting at a predetermined percentage of the nominal treatment time. In another embodiment, the increase in power commences at a derived time, rather than a predetermined time. Such derived time for increasing power may be based on prior measurements or determinations of how long it has taken the fill dose of medicament in the reservoir 115 to be depleted, as determined by sensor 217. These past measurements of reservoir depletion time may be stored in data repository 260 to determine the start time for increasing the power to aerosol generator 120, the rate at which power is increased, and/or the total duration of increase in power.

Upon determining that all medication has been used (e.g., by the sensor 217 detecting that all medication has been administered), the sensor 217 will send a signal to the controller 230, which in turn will send a signal to turn off power source 220. Thus, at operation 450 the treatment will end and the log in data repository 260 may be updated. The data repository 260 may store information about each treatment administered for a patient. The stored information in data repository 260 may be downloaded to a personal computer or other suitable device with a readable and writable memory. The information stored in the repository 260 may include, for each treatment, a total amount of actuation time of aerosol generator 120, a total amount of time spent inhaling by the patient, and/or total amount of time spent exhaling by the patient, among other things. In various implementations, one or more of the drug delivery actuation time (i.e., actuation time of the aerosol generator device or horn), the inhalation time, or the exhalation time may be rounded to a nearest second, for example.

As previously noted, the controller 230 may be used to perform various diagnostics for the patient or the device 200, which may be presented to the patient via a display 270. For example, when the treatment data within data repository 260 indicates that mesh 105 may be dirty, a signal may be sent by the controller 230 to the display 270 in order to visually depict the need to change the dirty mesh 105. In another example, the controller 230 may send a signal to display 270 to provide a visual indicator when the treatment data indicates that the patient has a poor breathing pattern, such that the patient can follow up with a medical practitioner or take other appropriate action. Furthermore, the log data in the data repository 260 may be used to perform various analytics or calculations to control subsequent treatments. For instance, treatment lengths may be calculated by controller 230 for a current treatment and/or one or more previous treatments, and the power level may be varied for subsequent treatments based on the calculations (e.g., an initial power level may be varied based on calculations from one or more previous treatments, or the calculations may be used to derive a schedule for controlling or otherwise varying the power level during a treatment, or other techniques may be used).

The controller 230 may also be used to aid therapists in assessing diagnostics of a patient's treatment, or to otherwise provide additional understanding regarding treatment, including whether poor mesh conditions necessitate interchanging of the mesh, or whether suitable mesh conditions indicate that the mesh can be changed later, among other things. For example, the treatment data in the data repository 260 may include information relating to the nominal mesh output rate (e.g., milliliters per minute) and medication chamber dose or volume (e.g., milliliters), which can be used to calculate a nominal amount of actuation time for a aerosol generator 120 at the nominal rate for a given treatment. For instance, a treatment may be designed to administer 6000 mL of medication at a nominal rate of 1000 mL/min (i.e., a six-minute treatment). Thus, the nominal amount of actuation time may be based on how many seconds the aerosol generator 120 (e.g., horn) should have been actuating during any given minute of the treatment.

As such, the total amount of nebulizer actuation time (e.g., horn-on time, or HOT) for each treatment may be compared to the nominal actuation time (e.g., nominal horn-on time, or nHOT), thereby providing an indication of whether the treatment was longer than expected because of a dirty mesh. Data may be further analyzed or correlated with subsequent treatments to reveal trends in mesh conditions (e.g., the trend may indicate that the mesh frequently becomes dirty after three uses, providing an estimate for when the mesh should be changed). Furthermore, treatment duration, in itself, may not provide an adequate measure of a dirty mesh because the duration does not account for influences attributable to a patient's breathing pattern, or to time spent not breathing (e.g., in between breaths), or other factors. Thus, dirty mesh conditions may be determined based on HOT as a percentage of nHOT (e.g., by dividing HOT by NHOT), or other factors, as HOT will only be affected by dirty mesh conditions or other factors that impact device output rate. For example, when the percentage HOT divided by NHOT exceeds a predetermined value (e.g., 200%), a dirty mesh can be assumed because increasing the power at the end of treatment failed to yield a treatment time within acceptable ranges, indicating that the mesh should be cleaned or changed. As will be apparent, the indication may be displayed on display 270 visually to indicate the need to clean or interchange the mesh.

Based on the foregoing, it will be apparent that a treatment may extend beyond the target treatment time because of a poor patient breathing pattern or because of a dirty mesh or other factor contributing to a reduction in device output rate. As such, the method described in FIG. 4 may actively monitor and compensate the breathing pattern, such that a treatment extending beyond the target treatment time may be attributable to the reduction in device output rate, which may be compensated for using the method described in FIG. 4. Therefore, either one or both of methods 300 and 400 may be active for any given treatment to compensate for these various factors, and which of the methods will be active may depend on settings of the device. It should be noted that controlling the power level based on patient breathing pattern in accordance with method 300 may be universally enabled for any aerosol treatment device, whereas controlling the power level to compensate for dirty mesh conditions in accordance with method 400 is primarily intended to be used with drug delivery devices that employ a mesh or other component that may deteriorate over time to thus cause a reduction in device output rate. It will also be appreciated that the settings may be based on any number of factors, or that a button or other selection mechanism could be used to enable/disable the power control algorithms, or other techniques may be used.

Further, in various embodiments, when simultaneously activating methods 300 and 400 for a treatment, method 300 will automatically terminate at a predetermined percentage (e.g., seventy-five percent) of the target treatment duration. In such a case, method 400 would take precedence over method 300 at that time. This is because method 300 dynamically accounts for variables relating to breathing pattern throughout the initial portion (e.g., the first seventy-five percent) of the treatment. Therefore, when the elapsed treatment duration exceeds the predetermined percentage of the target treatment duration (e.g., because the liquid drug has not been completely dispensed by that time), a dirty mesh can be assumed as being the reason for the longer treatment (e.g., exceeding target treatment duration can be attributed to a reduction in device output rate). As described above, ramping power up at the end of treatment should begin in advance of the treatment ending (e.g., to gradually increase the drug to be inspired), and therefore, method 400 will take precedence beginning at the predetermined percentage (e.g., seventy-five percent) of the target treatment duration.

Figure 5:
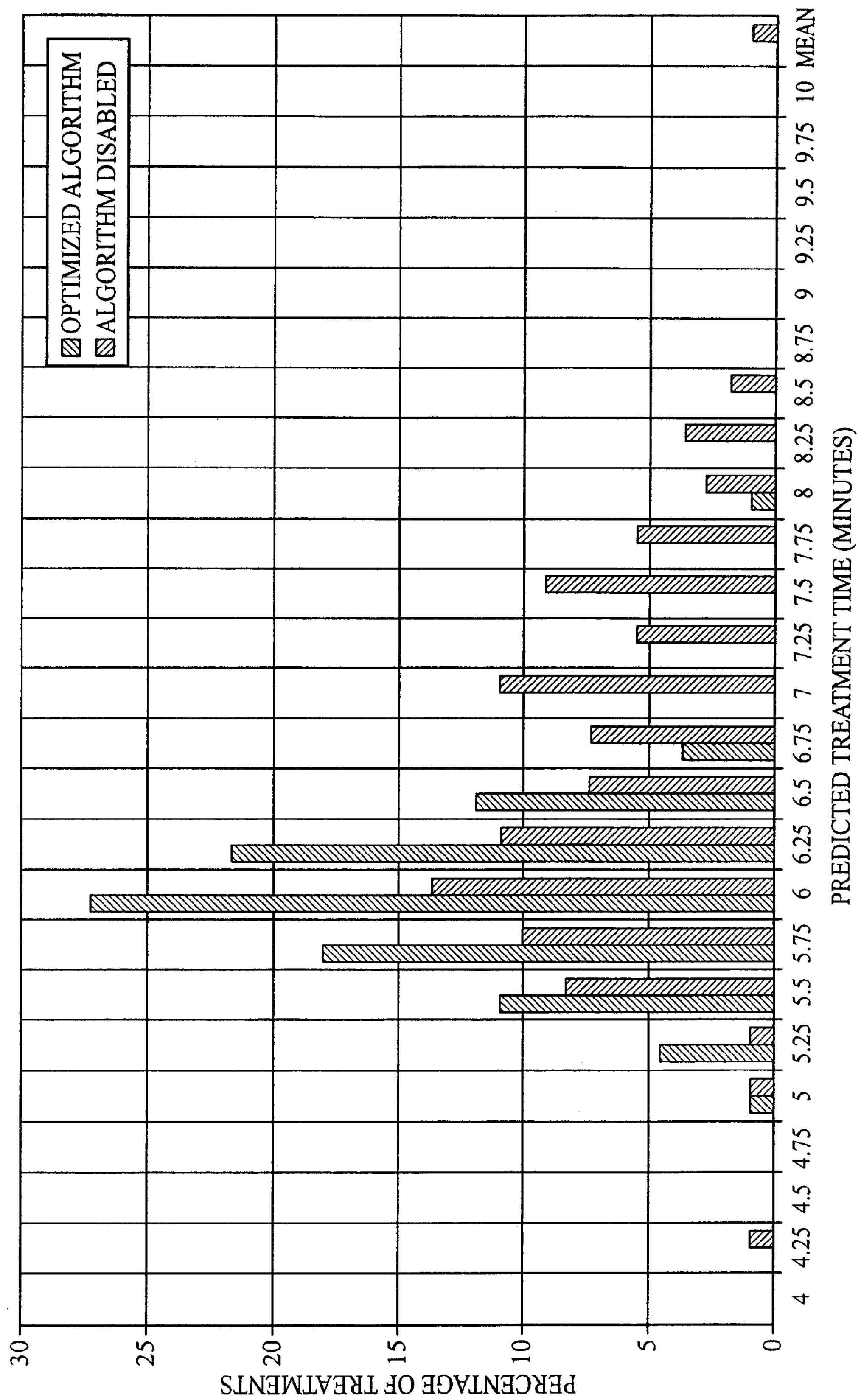
FIG. 5 illustrates a histogram comparing distributions of treatment times as a function of using a variable power algorithm according to various aspects of the invention.

Referring to FIG. 5, a histogram illustrates a comparison of distributions of treatment times as a function of using a variable power algorithm versus disabling the variable power algorithm. The histogram illustrated therein is based on experimentation using a database of approximately one hundred ten different breathing patterns. Based on a target treatment time of six minutes, when disabling the variable power algorithm, treatment times ranged from approximately four minutes, 15 seconds to eight minutes, thirty seconds (with a small percentage of treatments exceeding ten minutes). The mean treatment time with the variable power algorithm disabled was approximately 6.5 minutes, with a standard deviation of fifty-six seconds. By contrast, using the optimized variable power algorithm, most treatments completed between five minutes and six minutes, thirty seconds (with a small percentage exceeding six minutes, thirty seconds). As such, the variable power algorithm can be expected to significantly reduce the variability of treatment times and reduce mean treatment times of a representative population of patient breathing patterns. In particular, with the variable power algorithm enabled, the mean treatment time was reduced to approximately 5.9 minutes (a seventeen percent reduction), while the standard deviation was reduced to approximately twenty-four second (a fifty-seven percent reduction).

In another embodiment, the power may be adjusted based on a variety of other measured parameters other than those described above. For instance, sensor 217 may be configured to directly determine the liquid level within the reservoir 115 rather than for simply detecting treatment completion. Data repository 260 may include a table of values or calculator to determine the current desired liquid level to achieve a desired total delivery time. The current detected liquid level and the current desired liquid level at a given time may then be compared. If the current detected liquid level is less than the current desired liquid level, the power may be decreased. If the current detected liquid level is greater than the current detected liquid level, the power may be increased. The sensor 217 may have a variety of configurations; however, the present invention contemplates that sensor 217 may be a ultrasonic transducer configured to detect impedance changes, a resistive circuit configured to detect changes in resistance and/or current, a float switch, or any other liquid level detector known in the art. Alternatively, the liquid level may be inferred based on the amount of aerosol delivered to the patient. The amount of aerosol output from the drug delivery device 100 to the patient. For instance, the amount of liquid consumed may be determined by summing the concentration of aerosol output from the device over the delivery time period. The concentration sensor may be an optical concentration sensor, a particle sensor, or any other suitable concentration sensor known in the art.

Aspects and implementations of the invention described in the above disclosure may be described in terms of particular features, structures, or characteristics, but every aspect or implementation may not necessarily include the particular features, structures, or characteristics. Further, when particular features, structures, or characteristics are described in connection with an aspect or implementation, it is understood that it will be apparent to effect such features, structures, or characteristics in connection with other aspects or implementations, whether or not explicitly described. Thus, various changes and modifications to the above disclosure may be made, without departing from the scope and spirit of the invention. The specification and drawings, as such, are to be regarded as exemplary only, and the scope of the invention to be determined solely by the appended claims.

What is claimed is:

1. A method for maintaining a consistent treatment time for aerosol drug delivery treatments, comprising:

administering a predetermined dose of aerosolized drug to a patient using an aerosol generator, the aerosol generator operating in pulses to deliver the aerosolized drug to the patient in pulses, and the aerosol generator operating at an initial power level during a first set of pulses;

monitoring the patient's breathing pattern during the first set of pulses; and varying the power level at which the aerosol generator operates during a second set of one or more pulses based on the monitored breathing pattern in order to maintain the consistent treatment time, wherein the breathing pattern includes a ratio of the patient's inhalation with respect to exhalation, and wherein varying the power level includes increasing the power level for the second set of one or more pulses responsive to the ratio falling below a predetermined threshold during the first set of pulses.

2. The method of claim 1, further comprising:

determining a nominal treatment time for the treatment;

monitoring an elapsed treatment time for the treatment;

ceasing to vary the power level during pulses based on the monitored breathing pattern responsive to the elapsed treatment time reaching a predetermined percentage of the nominal treatment time; and increasing the power level at which the aerosol generator operates during pulses responsive to the elapsed treatment time reaching the predetermined percentage of the nominal treatment time.

3. The method of claim 2, wherein the nominal treatment time is a function of a predetermined dosage of a drug to be administered by the treatment and a nominal output rate for the aerosol generator.

4. The method of claim 2, wherein the predetermined percentage occurs at approximately 75% of the nominal treatment time.

5. The method of claim 2, further comprising increasing the power level at which the aerosol generator operates during pulses responsive to the elapsed treatment time reaching approximately 87.5%, 100%, and/or 125% of the nominal treatment time.

6. The method of claim 1, wherein the power level during the second set of one or more pulses is subject to a minimum level and a maximum level.

7. The method of claim 1, wherein the monitored breathing pattern includes a moving average of the ratio calculated over a predetermined number of the patient's most recent breaths.

8. The method of claim 1, further comprising storing data for the administered treatment to perform diagnostics relating to the patient's breathing pattern.

9. A method for maintaining a consistent treatment time for aerosol drug delivery treatments, comprising:

administering a predetermined dose of aerosolized drug to a patient using an aerosol generator, the aerosol generator operating in pulses to deliver the aerosolized drug to the patient in pulses, and the aerosol generator operating at an initial power level during a first set of pulses;

monitoring the patient's breathing pattern during the first set of pulses; and varying the power level at which the aerosol generator operates during a second set of one or more pulses based on the monitored breathing pattern in order to maintain the consistent treatment time, wherein the breathing pattern includes a ratio of the patient's inhalation with respect to exhalation, and wherein varying the power level for the second set of one or more pulses includes decreasing the power level responsive to the ratio exceeding a predetermined threshold during the first set of pulses.

10. An aerosol drug delivery apparatus, comprising:

a reservoir constructed to contain a predetermined dose of a liquid drug;

an aerosol generator in communication with the reservoir;

a power source arranged to deliver power to the aerosol generator, the powered aerosol generator producing an aerosolized form of the dose that can be administered to a patient;

a breath measuring mechanism operable to monitor the patient's breathing pattern during the administration of the dose; and at least one controller configured to control the power source such that power is delivered from the power source to the aerosol generator in pulses, the controller being configured such that (i) power is provided to the aerosol generator at an initial power level during a first set of pulses, and (ii) the power level is varied from the initial power level during a second set of one or more pulses based on the monitored breathing pattern in order to maintain a consistent treatment time for separate treatment sessions, wherein the breathing measuring mechanism includes a sensor operable to measure a ratio of the patient's inhalation with respect to exhalation, and wherein the controller is configured to vary the power level during the second set of one or more pulses by increasing the power level responsive to the ratio falling below a predetermined threshold during the first set of pulses.

11. The apparatus of claim 10, wherein the controller is further configured to administer the treatment by:

operating a clock when the treatment begins, the clock operable to monitor an elapsed treatment time for the treatment;

ceasing to vary the power level during pulses based on the monitored breathing pattern responsive to the elapsed treatment time reaching a predetermined percentage of a nominal treatment time; and increasing the power level at which the power source operates during pulses responsive to the elapsed treatment time reaching the predetermined percentage of the nominal treatment time.

12. The apparatus of claim 11, wherein the controller is further configured to increase the power level at which the power source operates during pulses responsive to the elapsed treatment time reaching approximately 87.5%, 100%, and/or 125% of the nominal treatment time.

13. The apparatus of claim 12, wherein the aerosol generator further includes an oscillating member constructed and arranged to vibrate the mesh and cause the liquid drug to be forced through the mesh apertures to form the aerosolized form of the drug.

14. The apparatus of claim 11, wherein the predetermined percentage occurs at approximately 75% of the nominal treatment time.

15. The apparatus of claim 10, wherein the aerosol generator includes a vibrating mesh having a plurality of apertures.

16. The apparatus of claim 15, wherein the nominal treatment time is a function of the predetermined dosage and a nominal output rate for the aerosol generator, the nominal output rate a function of the initial power level and a grading of the mesh.

17. The apparatus of claim 15, further comprising a data repository storing data for the administered treatment to perform diagnostics relating to a cleanliness or a dirtiness of the mesh.

18. The apparatus of claim 10, wherein the power level during the second set of one or more pulses is subject to a minimum level and a maximum level.

19. The apparatus of claim 10, wherein the controller is configured to obtain a moving average of the ratio calculated over a predetermined number of the patient's most recent breaths.

20. The apparatus of claim 10, further comprising a data repository storing data for the administered treatment to perform diagnostics relating to the patient's breathing pattern.

21. The apparatus of claim 10, wherein the controller includes electrical circuitry and a computer-readable medium containing computer-executable instructions.

22. An aerosol drug delivery apparatus, comprising:

a reservoir constructed to contain a predetermined dose of a liquid drug;

an aerosol generator in communication with the reservoir;

a power source arranged to deliver power to the aerosol generator, the powered aerosol generator producing an aerosolized form of the dose that can be administered to a patient;

a breath measuring mechanism operable to monitor the patient's breathing pattern during the administration of the dose; and at least one controller configured to control the power source such that power is delivered from the power source to the aerosol generator in pulses, the controller being configured such that (i) power is provided to the aerosol generator at an initial power level during a first set of pulses, and (ii) the power level is varied from the initial power level during a second set of one or more pulses based on the monitored breathing pattern in order to maintain a consistent treatment time for separate treatment sessions, wherein the breathing measuring mechanism includes a sensor operable to measure a ratio of the patient's inhalation with respect to exhalation, and wherein the controller is configured to vary the power level by decreasing the power level during the second set of one or more pulses responsive to the ratio exceeding a predetermined threshold during the first set of pulses.

* * * * *